ning; Marvin F. Matthews

United States Patent [19]

Thornton

[11] 4,375,674
[45] Mar. 1, 1983

[54] KINESIMETRIC METHOD AND APPARATUS

[75] Inventor: William E. Thornton, Friendswood, Tex.

[73] Assignee: The United States of America as represented by the Administrator of the National Aeronautics and Space Administration, Washington, D.C.

[21] Appl. No.: 198,093

[22] Filed: Oct. 17, 1980

[51] Int. Cl.³ .................. A61B 5/05; G09B 19/00; H04N 7/18

[52] U.S. Cl. .................. 364/559; 364/522; 364/413; 73/379; 128/782; 358/105

[58] Field of Search .............. 358/105, 108, 125, 126; 364/559, 522, 525, 413, 560–564; 73/379; 128/782, 774

[56] References Cited

U.S. PATENT DOCUMENTS

| | | | |
|---|---|---|---|
| 3,973,332 | 8/1976 | Slomski | 73/379 X |
| 4,112,463 | 9/1978 | Kamin | 358/105 |
| 4,128,316 | 1/1980 | Nilsson et al. | 128/782 X |
| 4,136,387 | 1/1979 | Sullivan et al. | 364/525 X |
| 4,137,566 | 1/1979 | Hass et al. | 364/515 X |
| 4,146,924 | 3/1979 | Birk et al. | 364/513 |
| 4,163,941 | 8/1979 | Linn, Jr. | 364/410 X |
| 4,172,661 | 10/1979 | Marcus et al. | 364/460 X |
| 4,197,855 | 4/1980 | Lewin | 128/653 |
| 4,236,180 | 11/1980 | Cayzac | 358/105 |
| 4,238,828 | 12/1980 | Hay et al. | 364/559 |
| 4,281,342 | 7/1981 | Ueda et al. | 364/559 X |
| 4,307,608 | 12/1981 | Useldinger et al. | 73/379 |

Primary Examiner—Edward J. Wise
Attorney, Agent, or Firm—Edward K. Fein; John R. Manning; Marvin F. Matthews

[57] ABSTRACT

Disclosed are apparatus and method for the determination of functional capability of bodies. Reach as well as velocity, acceleration and force generation at various positions may be determined for a body by a three dimensional kinesimeter equipped with an ergometer. A general data package indicative of performance potential of a subject body or collection of bodies is provided for interfacing with data characteristic of various environments.

27 Claims, 15 Drawing Figures

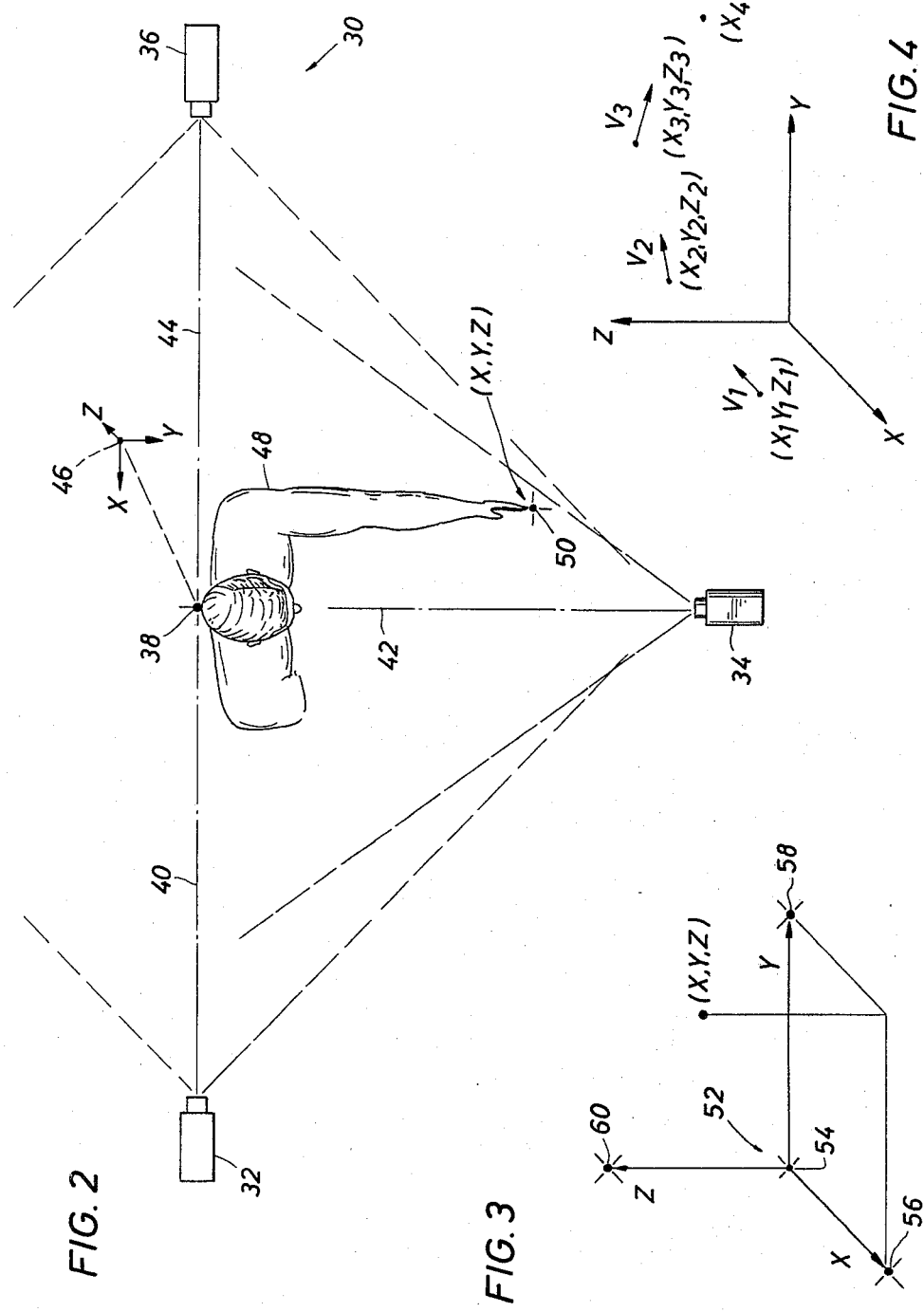

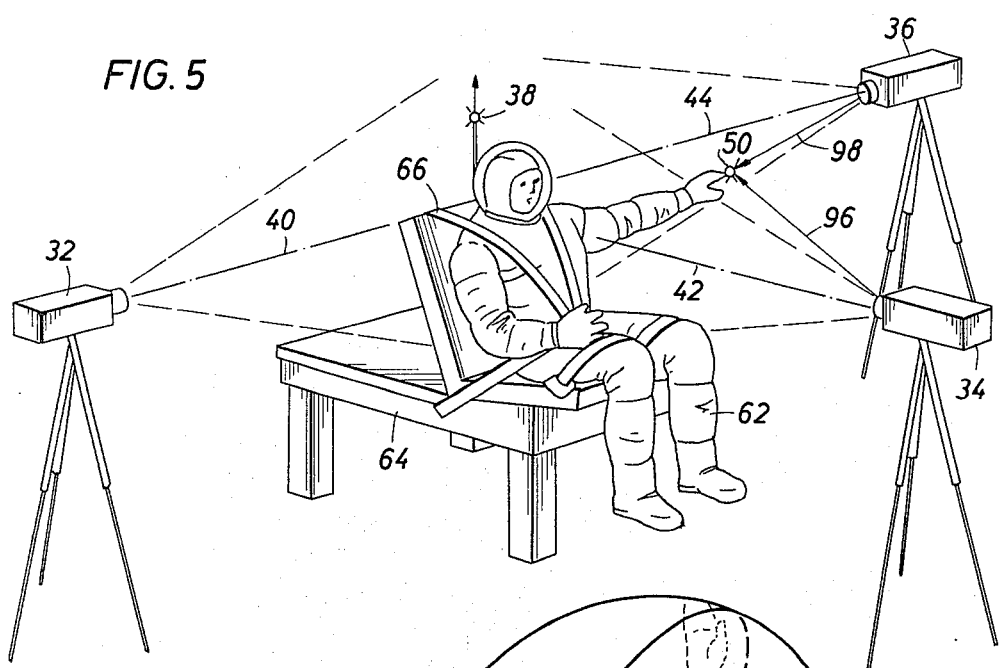
FIG. 5
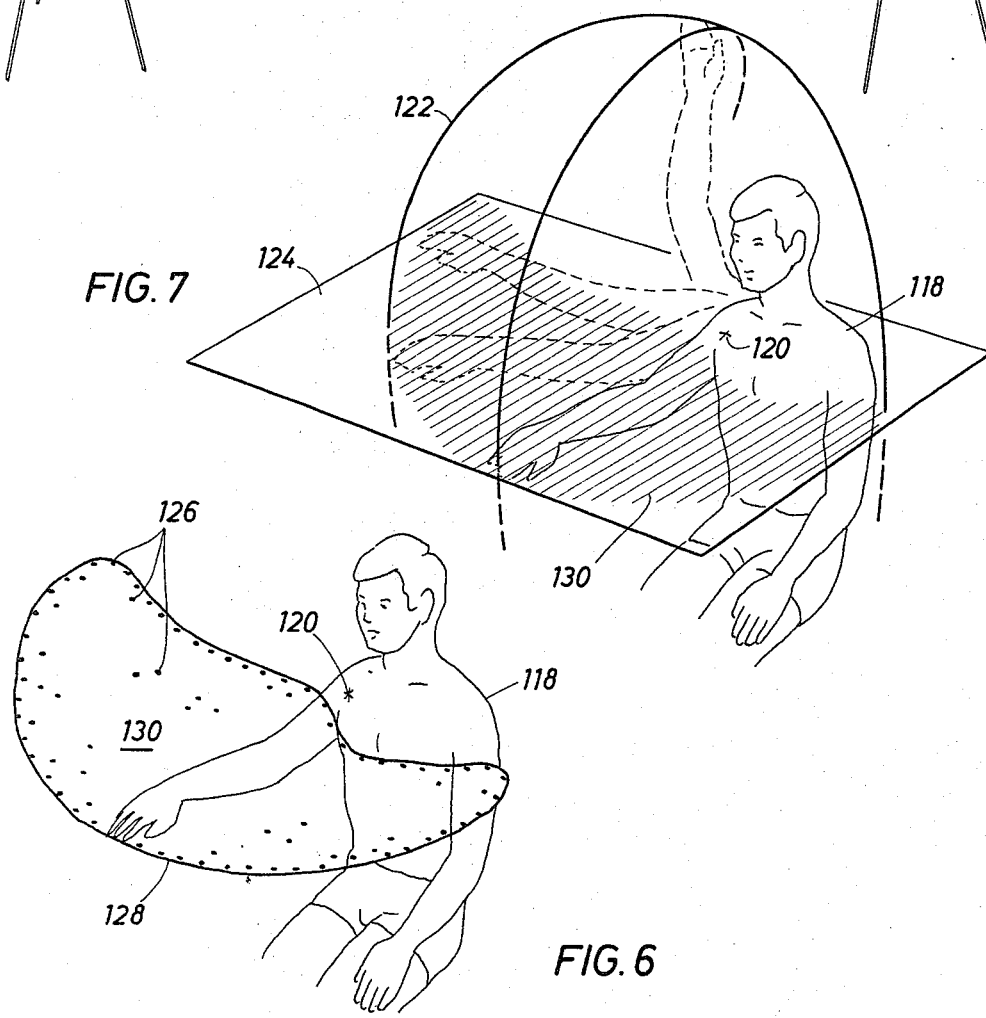
FIG. 7
FIG. 6

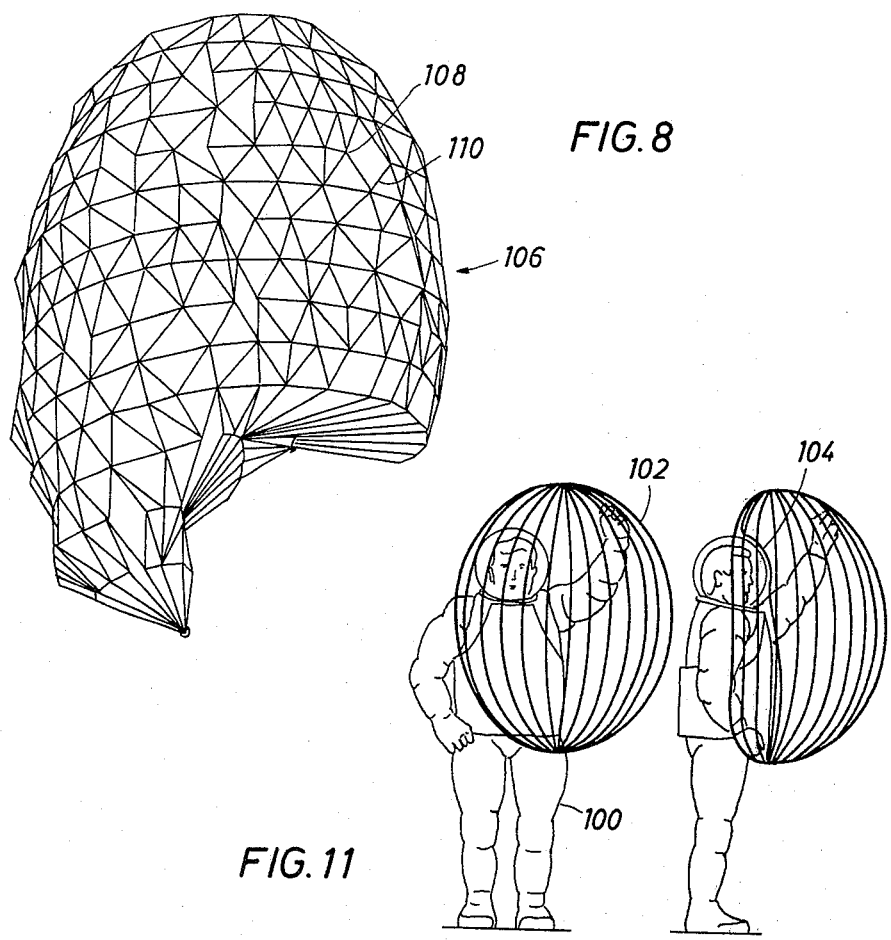
FIG. 8
FIG. 11
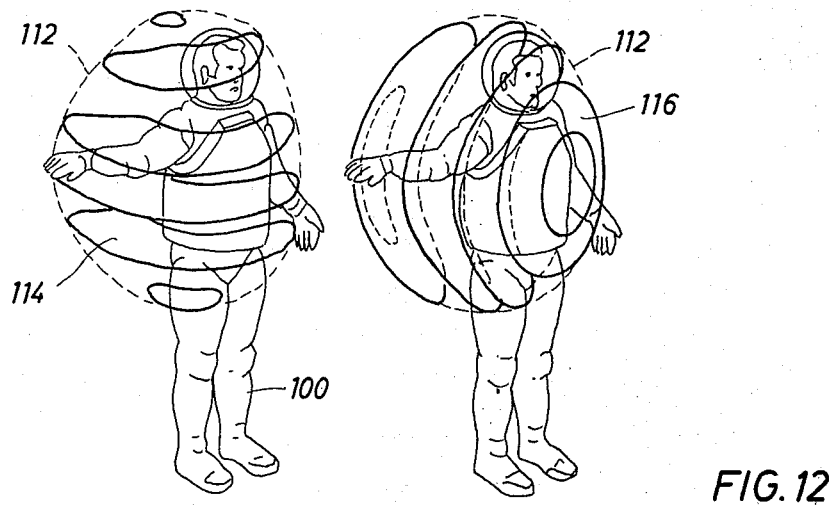
FIG. 12

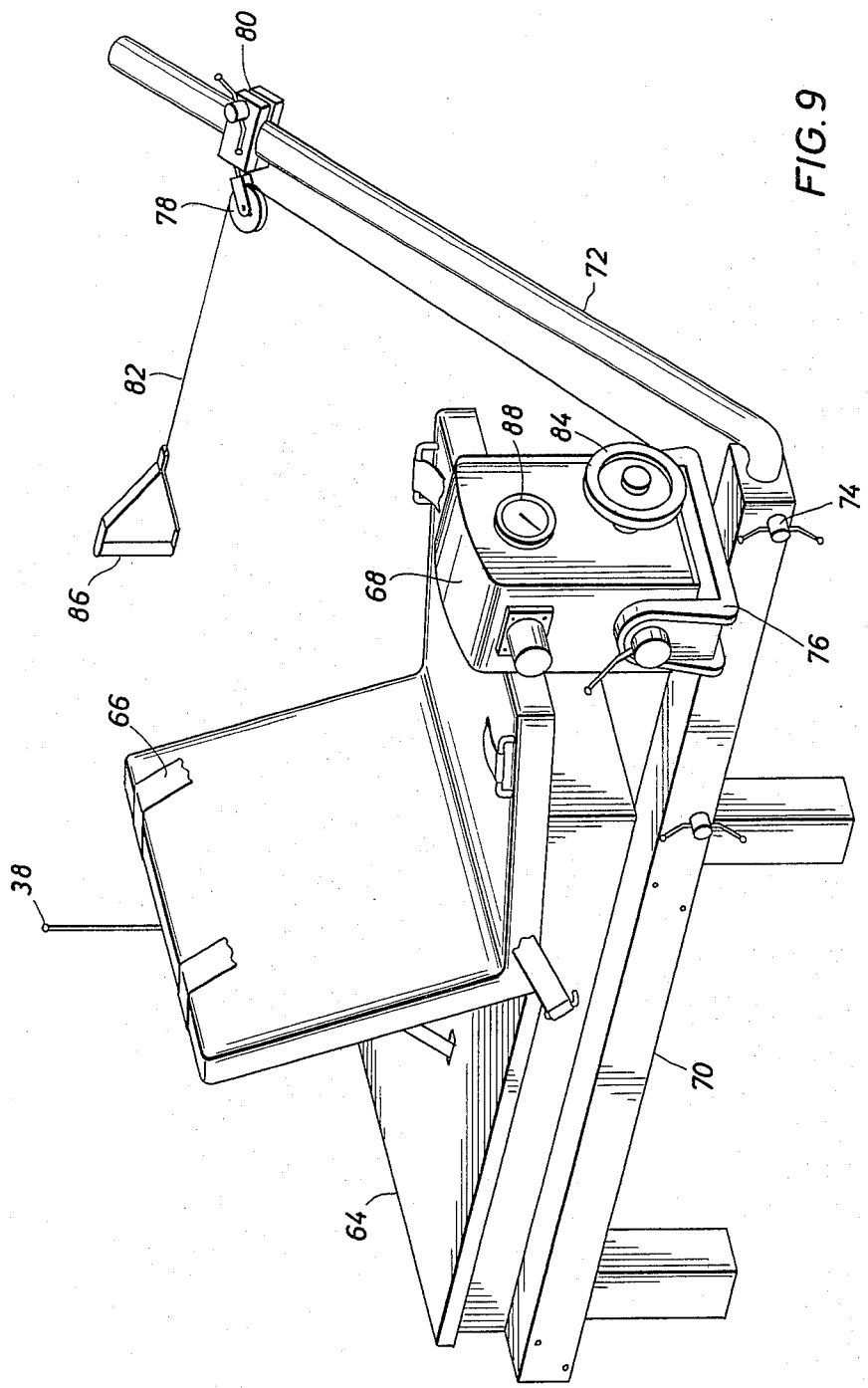

KINESIMETRIC METHOD AND APPARATUS

ORIGIN OF THE INVENTION

The invention described herein was made by an employee of the United States Government and may be manufactured and used by or for the Governement of the United States of America for governmental purposes without the payment of any royalties thereon or therefor.

BACKGROUND OF THE INVENTION

1. Field of the Invention

The present invention pertains to methods and apparatus for the determination of functional capability of bodies. More particularly the present invention relates to systems and techniques for quantitatively measuring the range of movement of which subjects, including human subjects, are capable, as well as the extent to which such subjects are capable of functioning at various attitudes. The present invention finds particular application to the measurement of human body movements and performance potential, including reach parameters and task-performing capabilities, the accumulation of such data and the presentation of such information for interfacing with design information characteristic of various environments. The anthropometric data acquisition available by means of the present invention may be utilized to accommodate and improve the interface between human subjects and various machines and work places including, for example, cockpits and cabins of spacecraft and other such confining and demanding environments.

2. Description of Prior Art

It is generally advantageous to improve the interface between man and his environment in various settings, and particularly work places where a subject or operator is required to perform various tasks. In some cases, it is critical to the comfort and safety of the human operator, as well as the efficiency of performance of the man/machine combination, that the work place be complementary to the performance capability of the operator. Since human body designs are generally fixed, to achieve a proper accommodation between man and machine the design of machines and work spaces may be altered where necessary. To determine environment design requirements to achieve a proper accommodation, it is first necessary to acquire human anthropometric and kinesimetric data in physical terms that may be applied to such machine and environment design. To characterize motion of human body segments in physical terms requires the essentially continuous measurement without mechanical interference of location in three dimensions, velocity, acceleration and force exertion of selected body points.

The description of the motion of the human body has previously been a tedious, expensive and time consuming procedure carried out usually manually, and has never been complete. Further, such measurements have never combined the two essentials of muscle activity, namely, motion and force. The usual procedure has been to measure a sample population of subjects for some particular aspect of motion of interest. In some cases, particularly where complex tasks are required, a mock-up of a proposed design is obtained and a representative sample of the prospective user population is placed in the mock-up to go through the required interface tasks.

A variety of techniques have been developed to attempt to measure one aspect or another of human activity. Generally these techniques require various degrees of manual data reduction to obtain quantitative results. Chronophotography techniques are known for motion study. However, while such techniques can be extended to three dimensions with the use of stereo cameras, such an approach is best limited to a single action, and requires extensive manual data reduction.

Various mechanical devices, including cable or rod arrangements, have been utilized to track an anatomical point and record its path within limitations, such as those defined by mechanical interference. I have previously devised a method of continuously registering the angle of a goniometer to allow it to continuously follow varying limb angles.

Various sonic, ultrasonic and electromagnetic radiators have been used to track points. Multiple receivers may be utilized, and the path of a radiator determined by the phase differences between the signals detected by the several receivers.

Video cameras have been used to record space location and motion patterns. The cameras detect light from reflective strips on dark-suited subjects, or from light sources including infrared light emitting diodes attached to various parts of the subject. Computer software has been used to analyze data from optical sensors. A computer approach has also been used to generate a synthetic man model based on static measurements from individuals. However, such a system is complex and expensive, and its accuracy and reliability are limited by available knowledge of the human body as a mechanical device.

Force and torque measurements have been made using various ergometers. A known cable tension arrangement allows only a static isometric determination of force at a single point. An isometric system using a fixed force, provided usually by weights, could be moved through a range of motion. Such systems, however, are limited to the maximum weight which can be moved at the "weakest" point of the range of motion. An improved isokinetic ergometer allows continuous measurement over a range of motion and torque, and over a range of speeds from a static, or isotonic, configuration to the maximum speed of which a body is capable.

A prior system combining force and position studies was directed to torques effected at human joints driven by external forces. Body limibs were rigidly attached to goniometers and driven through arcs with the resisting forces being measured.

Prior kinesimetric techniques have been characterized by the very limited amount and special nature of the data gathered as well as considerable time and expense needed to gather the data. Such known systems have not acquired complete data, that is, with force measurements combined with motion measurements including position, velocity and acceleration. Nor has such information been stored or displayed in a practical format utilizing engineering quantities.

Quality of the man/machine interface frequently determines performance of the man/machine unit, which often overrides performance of the machine design or the ability of the operator. This interface becomes increasingly important with machines of greater complexity and higher performance, particularly in the space program where machines and men are often operated beyond customary performance limits. Operations in a space environment are also complicated by variations in gravity, weightlessness, and alterations in size and shape of human bodies due to weightlessness.

An automatic video goniometer has been developed for the measurement of active body angles. The video goniometer includes a video camera, a master control with a microprocessor and a standard typewriter/terminal. A series of jigs containing coded point sources of illumination are attached to a movable body segment. The body segment is placed at one extreme of motion and its axis angle is measured either with respect to a local vertical or to a second reference axis. Measurement of the reference points on the video raster is effected automatically. Measurement of the segment axis angle at its other extreme of motion is similarly made. The miroprocessor calculates and presents the angular value.

Further aspects and details of advances in the field of anthropometry are discussed in "Measurement and Control of Human Movement", a collection of presentations by H. J. Woltring published in the Netherlands.

SUMMARY OF THE INVENTION

The present invention provides method and apparatus for determing the functional capability of bodies and body segments. A position detector includes sensor means for detecting the location of body points in space and for tracking the movement of such points in three dimensions relative to a frame of reference. The operation of the sensor means may be automatically controlled, and the data obtained from the sensor means may be appropriately processed and/or stored. Means are also provided whereby the ability of a subject body to exert force in specified directions and at specified locations may be determined. The force-capability measurements may be conducted in conjunction with the tracking of the subject body, and the force data combined with the position and tracking data to provided a comprehensive presentation of the functional capability of the subject body.

Means are provided for interfacing the compilation of the data characteristic of the functional capability of the subject body with design data characteristic of environments, including objects such as machines and work spaces and the like.

The presentation of the data reflective of the subject body functional capability may be varied, and generally includes position, or reach, information, velocity and acceleration information characteristic of the mobility of the subject body at various locations, and information descriptive of the ability of the subject body to exert force and/or torque at various locations, in various directions and even at various speeds. Each of these types of information may be presented, for example, as a function of location in the form of iso-contours including trajectories, closed and/or partial envelopes, and intersections of trajectories and/or envelopes with surfaces such as planes.

In a particular embodiment described and illustrated, a position detector includes two or more optical sensors such as video cameras, arranged for the definition of a frame of reference with respect to which the video cameras may locate the position of a subject body. An anatomical point on the subject body, or collection of such points, may be detected and tracked by the video camera system by means of an incandescent lamp or lamps fixed to the point or points in question. System control and data acquisition means generally operate the video cameras and, if need be, the lamps, and controls the acquisition of the data obtained from the camera system.

An ergometer is provided for obtaining quantitative measurement of the amount of force that may be exerted by a subject body at specified locations and in specified directions. In a particular embodiment described and illustrated a dynamometer is utilized in the ergometer. The force measurement data is combined with the position and tracking data by the data acquisition means. The output data stream from the data acquisition means may be stored for future use or employed effectively on-line in the presentation of information characteristic of the functional capability of the subject body. Such quantitative information may be calculated by a data processing system.

The same data processing system which calculates the performance potential information of the subject body may be utilized to interface such information with environment design information. Alternatively, a separate data processing system may be used for such interface analysis.

The present invention provides a three-dimensional anthropometric system including a computer-based data collection system in conjunction with computer processing to produce automated measurements of body segment position, force generation, velocity and acceleration.

The present invention may be utilized to determine the performance potential of essentially any type of moving body, whether human or nonhuman, and whether living or mechanical. While the present invention is particularly applicable to the study of human functional capabilities, the present invention may be similarly employed to determine the performance potential of various machines and mechanical devices, including robots.

BRIEF DESCRIPTION OF THE DRAWINGS

FIG. 2 is a plan view of the video camera/light position location system;

FIG. 3 illustrates the identification of a point in an orthogonal coordinate system;

FIG. 4 illustrates the location of four points and three velocity vectors in the coordinate system;

FIG. 5 is a perspective view of the video camera position detection system with a subject in place;

FIG. 6 is a perspective view of a subject, with a horizontal plane superimposed and including points of intersection representative of the subject's left arm and hand reach;

FIG. 7 is a view similar to FIG. 6, but further illustrating the location of a plane intersecting the maximum reach envelope of the subject body;

FIG. 8 is a perspective view of a right arm and hand reach strophosphere;

FIG. 9 is a perspective view of a portion of the force measurement system, including an isokinetic dynamometer;

FIG. 11 includes front and side elevations of a subject executing vertical arm sweeps, with reach sweep lines superimposed;

FIG. 12 includes two perspective views of a subject with horizontal and vertical transverse plane intersections of the reach envelope superimposed;

DESCRIPTION OF PREFERRED EMBODIMENTS

Figure 1:
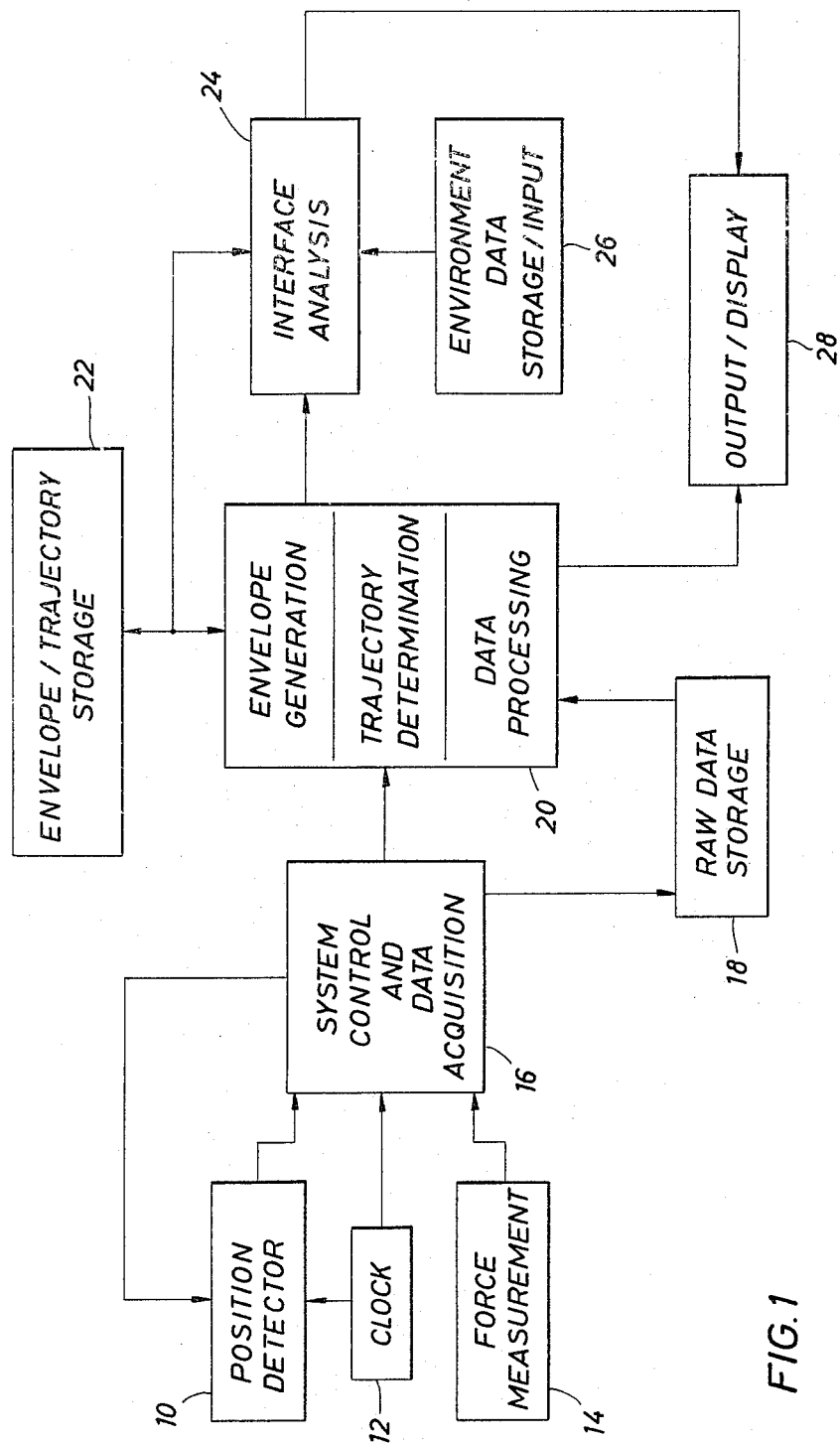
FIG. 1 includes a functional block diagram of a kinesimetric system according to the present invention.

Features of the present invention are illustrated by means of a functional block diagram in FIG. 1. Position and motion of a subject body relative to a reference system are sensed by a position detector 10. A timing device, such as a clock 12 which may be an electronic oscillator, is provided to either command the times at which positions of the subject body are sensed by the position detector 10, or to tag the data obtained by the position detector to thereby establish the data as a function of time, or to perform both of these operations. A force measurement system 14 is provided to sense the force-exerting exerting capability of a subject body operating at various positions and in various directions, for example. Force data is obtained simultaneously with position and time data from the position detector 10 and the clock 12, respectively.

A controller 16 is provided to operate the position detector 10, and to effect inital processing of the data from both the position detector and the force measurement apparatus 14. Any appropriate control and data acquisition system may be utilized at 16 for these purposes. For example, a Rockwell RC502 microprocessor-based control unit may be employed in the system 16. Details of the function and operation of the control and data acquisition system 16 are discussed hereinafter. The output from the control and data acquisition system 16 is in the form of a data stream which may include both force measurement and position data. The raw data stream may be recorded for storage by any conventional means 18, or may be transferred on-line to a data processing system 20.

The data processing system 20 may include a general purpose computer, or may be a special purpose device. For example, a Data General Eclipse S/230 computer may be utilized for this purpose. The data processing unit 20 receives the raw data stream and determines point trajectories of the subject body, calculates values of velocity and acceleration of the body along the trajectories, and determines the values of force exerted by the body at various locations. The data processing unit 20 also derives selected reach envelopes characteristic of the subject body. Iso-contours of velocity, acceleration and force may also be determined by the data processing system 20.

The derived envelope and trajectory data produced by the data processing unit 20 from the raw data stream may be stored by conventional means 22 for further use by the data processing unit, or for later use to develop mathematical interfaces between trajectory and/or envelope information of the subject body and corresponding information characteristic of selected environments. Alternatively, the derived subject data may be used on-line in such interface analysis procedures.

The interface analysis function at 24 may be carried out by means of an additional computer and appropriate software, or by a subsystem of the data processing unit 20. Data characteristic of one or more selected environments to be interfaced with the processed data stream characteristic of the subject body may be provided at 26 by any conventional information storage facility, such as by tapes or discs, or from input apparatus, such as a keyboard terminal, or from any other appropriate source.

One or more output devices 28 may be provided to present results of the interfacing process from the system 24, or the processed envelope, trajectory or other information from the data processing system 20. Such output devices may be display units for providing digital and/or graphical presentations of data, and may include printers, plotters, or cathode ray tube units, for example.

The position detector 10 may include any system with the capability of locating and tracking a point in three dimensions. For example, an optical system may be utilized employing optical sensors arranged to view a subject under examination from two vantage points. The two optical sensors may be oriented so that the center lines of their respective fields of view intersect at a point, for example. In such case, the center lines define a plane in which the two optical sensors lie. Generally, by "triangulation", or equivalent techniques, the location of any point in the plane thus defined may be determined by combining the location of the point along the plane as determined by the individual optical sensors. Also, the distance the point may be located off of the plane may be simularly observed by the sensors, and the perpendicular distance between the point and the plane noted. In this way, the location of such a point may be determined in three dimensions by reference to the plane defined by the center lines of the fields of view of the two optical sensors and the point of intersection of the center lines serving as an origin, and to the distance above or below the plane at which the point may be located. The location of the point in space may also be related to a reference point for convenience, whose location in the frame of reference is known. Generally, any convenient frame of reference may be utilized, as long as the sensing of the position of the point in question on the subject body by the sensors may be determined and related to the frame of reference.

By way of illustration rather than limitation, a three-dimensional frame of reference may be defined by an orthogonal XYZ coordinate system as shown in FIG. 3, wherein a point in space is located with respect to the coordinate system by appropriate identification of the point coordinate values (X,Y,Z) in the usual manner. If, for example, an optical sensor were located along the X axis, and a second optical sensor were located along the Y axis, with both sensors oriented so that the center lines of their respective fields of view were coincidental with the X and Y axes, respectively, the center lines would intersect at the origin of the coordinate system, and define the XY plane. Location of the projection of the point in the XY plane by the optical sensors would yield corresponding coordinate values in that plane. Elevation of the point location above or below the XY plane determines the value of the Z coordinate for the point location.

Optical sensors for use in providing the position detector 10 may include video cameras. In such case, for example, a video camera positioned along the X axis in FIG. 3 with the field of view centered on the origin would detect the point (X,Y,Z) illustrated therein in the upper right hand quadrant of the camera's field of view. Similarly, the video camera similarly positioned and oriented along the Y axis would detect the same point located in the upper left hand quadrant of the field of view of that camera. A vector may be constructed from the X axis camera to the point (X,Y,Z). A second vector may be constructed from the Y axis camera to the same point. Effectively, the data processing system 20, utilizing the identification of the two video cameras with respect to the origin of the XYZ coordinate system, would combine the information provided by each of the cameras indicating where the respective camera determines the point in space to be located, and locate that point at (X,Y,Z) relative to the coordinate system.

While a frame of reference for locating a point in three dimensions may take any convenient form for use in the present invention, by way of illustration rather than limitation, an orthogonal frame of reference defined by optical sensors is considered hereinafter. Additional optical sensors may be used where convenient or necessary to ensure that the point or points to be located by the position detector will always be within the field of view, or sensing, of at least two sensors arranged to define a plane.

The point or points to be located and tracked must be detectable by the sensors. In general, where the sensors are electromagnetic radiation detectors, the points to be detected must be capable of emitting radiation within the frequency and intensity ranges detectable by the sensors, and wherein the sensors may appropriately distinguish the emitters from the background. For example, video cameras may detect and track light sources, particularly against a background of sufficiently low intensity to permit the video cameras to distinguish the light source. Small incandescent lamps approximating point sources may be utilized to identify the point or points to be located and tracked by the camera system.

A three-camera video position detector system is illustrated at 30 in FIG. 2. The three cameras 32, 34 and 36 are located in a single plane, and positioned equidistant from a point, shown occupied by a light source, such as an incandescent lamp 38. The center lines 40, 42 and 44 of the cameras 32, 34 and 36, respectively, pass through a common point in the plane of the cameras, with the center lines 40 and 44 being coincidental and at right angles to the center line 42. Then, the cameras 32-36 define an orthogonal coordinate system if camera 32 is considered to lie with its center line 40 along the positive X axis, and camera 34 is considered to lie with its center line 42 along the positive Y axis. The third camera 36 is then positioned with its center line 44 along the negative X axis. The Z axis is perpendicular to the plane defined by the lines 40-44, with the reference lamp 38 positioned along the Z axis, and possibly at the origin. The light source 38 may lie in the plane of the three cameras, and identify the origin of the frame of reference defined according to the positions and orientations of the cameras. The frame of reference thus defined is identified by the XYZ coordinate system 46, which is shown displaced for purposes of clarity and convenience. Generally the reference lamp 38 may be offset from the coordinate axes, and is shown here along the Z axis as a convenient arrangement.

Generally, any type video camera may be utilized in the camera system 30. For example, each of the cameras may be a RCA Model TC-1000 camera, modified if necessary to synchronize the raster scans of the three cameras as discussed hereinafter.

A subject, such as the person 48, whose anthropometric characteristics are to be observed, is positioned generally within the field of view of each of the cameras in the camera system 30. If, for example, the left arm functional capability of the subject 48 is to be examined, a detectable light source, such as an incandescent lamp, 50 is fixed to the end of the left arm. Then, as the left arm is moved about as described hereinafter, the location of the light source 50 is detected and tracked by the camera system 30. It will be appreciated that the arm of the subject 48 may, at times, be positioned so that one or the other of the X-axis cameras 32 and 36 may be blocked by the subject body from receiving light emitted by the light source 50. However, at least one of the X-axis cameras 32 and 36 may be expected to be in position to detect the light source 50 so that the lamp 50 may be detected by at least two cameras at all times. The position detector 10 is thus operated by the control and data acquisition system 16 to acquire position data at all times from the front camera 34, and from either of the side cameras 32 or 36, as the position of the light source dictates. Thus, if one of the X-axis cameras 32 or 36 is blocked from sensing the light source 50, the other of these two cameras will be receiving light and generating data under the control of the data acquisition system 20. In situations wherein the light source 50 is detected by both X-axis cameras 32 and 36, the control system 20 may operate to avoid redundancies, and choose to forward position data from that X-axis camera to which the light source 50 is closer at the time.

Prior to the examination of a subject body, the position detector 10 may be calibrated with a standard four-lamp system shown generally at 52 in FIG. 3. The lamps are arranged and positioned with one lamp 52 at the origin and one lamp (56, 58 and 60) along each of the three orthogonal axes of the XYZ coordinate system as illustrated. The lamps 56-60 positioned along the axes are equidistant from the origin lamp 54. Additionally, the distance between the origin and each of the axis lamps is known. The lamp system 52 is thus arranged coincident with the coordinate system defined by the location of the video cameras 32-36. Additionally, the distance from the origin to each of the video cameras is known. For convenience in scaling data as discussed hereinafter, each of the axis lamps 56-60 may be located a unitary distance from the origin lamp 52, such as one foot. The lamp system 52 then defines a unitary cube.

Each of the four lamps 54-60 is lightly individually and on command by the system control 16, and the lamps are detected by the cameras 32-36. The detected locations of the lamps, whose positions in the frame of reference are known, are stored. This calibration procedure allows the data processing system 20 to be appropriately programed with proper scale factors and locations, as well as a zero reference used in calculations of position for accurate dimensional measurements. The calibration procedure also provides for the correction of possible errors introduced by inequalities in the camera lens systems, or camera spacing differences among the three video cameras 32–36. One of the lamps 54–60 may serve as the reference lamp 38 of FIG. 2, for example. Alternatively, a fifth reference lamp 38 may be used, with its location relative to the frame of reference provided by the lamps 54-60 noted and stored in the calibration stage.

The lamps may be mounted on the subject and in the reference system array in any suitable manner. As part of the calibration procedures, the video threshold of each video camera 32-36 may be adjusted to detect the lamps mounted on the subject body and the reference lamp or lamps, and virtually none of the background. This operation assures a minimum of ambient influence from light sources other than the reference and subject lamps, and also assures that the position detector system 10 is viewing the reference and subject lamps as the brightest elements on the video screens. The system control and data acquisition apparatus 16 includes a video threshold comparison circuit for determining the video threshold for each of the cameras, and storing the threshold value for each camera in operation. The control system 16 also may be utilized to operate the reference and subject lamps. In cases in which only one subject lamp is used, such as lamp 50 as illustrated in FIG. 5, the subject lamp may be operated continuously. Where two or more subject lamps are used, however, the lamps may be flashed individually and in sequence, with the video cameras detecting the location of each lamp in turn in the sequence. However, such a time-sharing approach to the acquisition of data from multiple points is but one technique that may be utilized. Similarly, the reference lamps used during the calibration process may be flashed in sequence, with the camera system calibration operation appropriately synchronized.

In FIG. 5 the three video cameras 32-36 have been arranged as in FIG. 2, and the system calibrated as described. The lamp system 52 has been removed, leaving a single reference lamp 38. A space-suited subject 62 is positioned on a bench, or seat, 64 fixed with respect to the reference lamp 38 and generally within the field of view of each of the cameras 32-36. The bench 64 is fitted with restraints 66 which are used to generally confine the subject 62 fixed relative to the reference lamp 38 except for the subject body portion or portions whose function is to be examined. In the case illustrated, the subject 62 has been fitted with a subject lamp 50 fixed to the extremity of the left arm so that reach, movement and strength of the left arm and hand may be examined. With the torso of the subject 62 fixed relative to the reference lamp 38, the functioning capability of the left arm and hand relative, for example, to the upper body may thus be evaluated.

In FIG. 9 the bench 64 has been modified to add an ergometer, shown here including a dynamometer 68. A generally tubular member 70 is mounted along the right side of the bench 64, and receives a right angle member 72. The right angle member 72 may be rotated about the longitudinal axis of the tubular member 70 to a selected orientation, and locked in such configuration by hand-tightened bolts 74 in appropriate threaded holes in the tubular member. The dynamometer 68 is mounted on the tubular member 70 by means of a swivel 76 which permits the dynamometer to be oriented in a range of selected directions, and locked in any such configuration. An idler pulley 78 is positioned and adjustable along the right angle member 72 and locked thereto by a bolt-tightened bracket 80. A cable 82 is wound about the capstan 84 of the dynamometer 68, and passes through the idler pulley 78. A hand grip 76 is fixed to the end of the cable 82.

Generally, any type of ergometer may be employed with the present invention. For example, a CYBEX II Isokinetic Dynamometer may be utilized whereby the value of force by which a subject pulls on the cable 82 at a constant, preselected speed is displayed on the gauge 88 and transmitted to the data acquisition system 16. Isokinetic force generation capability is a particularly meaningful and useful characteristic to measure with the kinesimeter. However, any type of force measuring device may be used.

Figure 10:
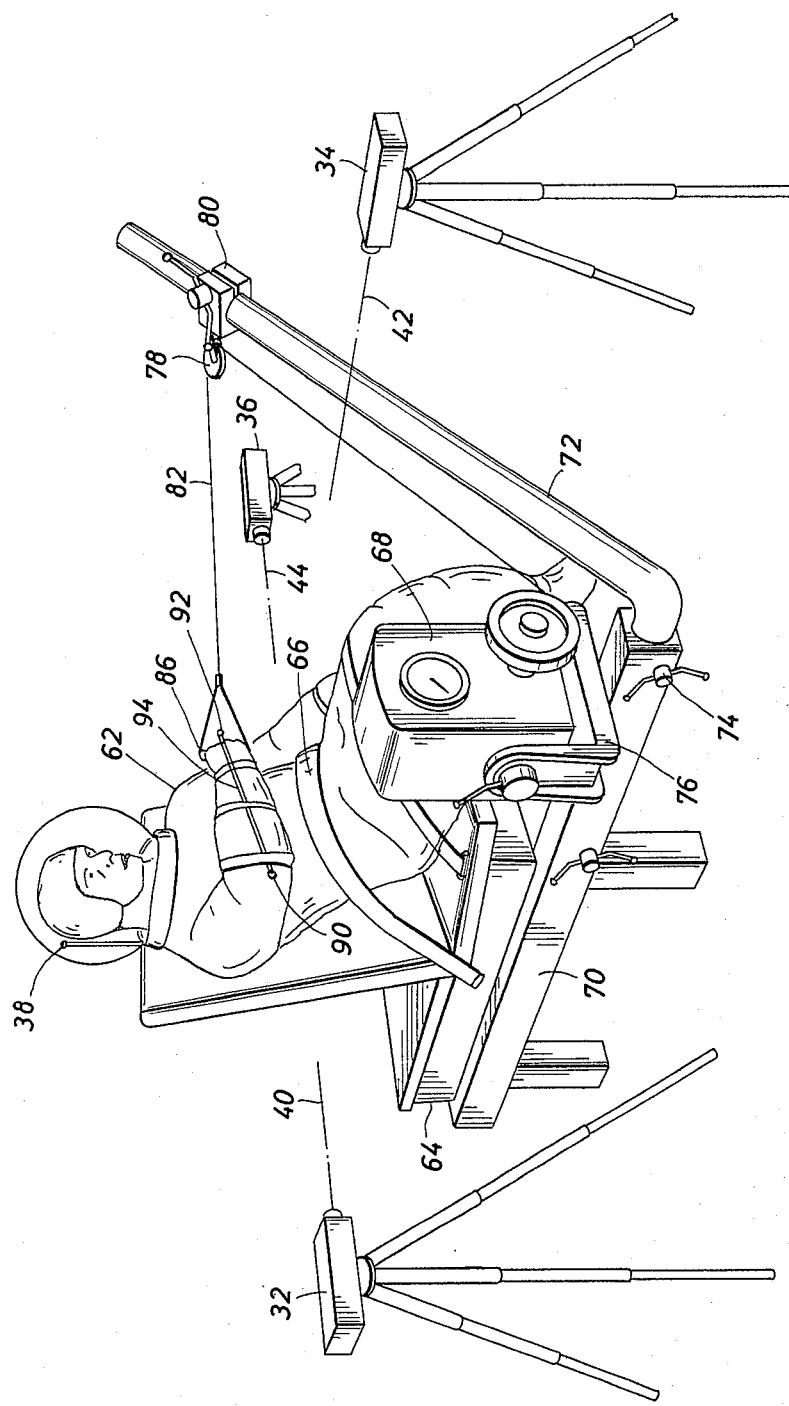
FIG. 10 is a perspective view of the force measurement system indicated in FIG. 9 in conjunction with the video camera arrangement, and with a subject in place.

In FIG. 10 the space-suited subject 62 is again shown positioned and restrained in the bench 64 within the three-camera system with the reference lamp 38 in place. The ergometer arrangement of FIG. 9 has been added, and the subject 62 is illustrated pulling on the ergometer cable 82 by means of the handle 86. Two subject lamps 90 and 92 are positioned at the right elbow and right hand, respectively, of the subject 62 whereby the camera system may locate and track these two anatomical points, thereby locating and tracking the right forearm of the subject as the subject exerts measured forces in a particular direction. The separation of the lamps 90 and 92 is maintained by a generally rigid connecting member 94, which may include electrical conducting elements for operating one or both of the lamps. The connector 94 is strapped to the subject forearm as illustrated.

The subject 62 exerts measurable forces on the ergometer system by pulling on the cable 82. The idler pulley 78 may be positioned in any desired location to permit the subject to exert such a pulling force in any selected direction, and at any selected location. For example, by mounting the ergometer system on the bench 64 so that the right angle member 72 is positioned generally behind the seated subject 62, the idler pulley 78 may be positioned so that the subject may pull in a generally forward direction, that is, toward the front camera 34, to exert measured forces in a direction opposite to that indicated in FIG. 10. The ergometer system may be positioned and/or extended to allow a subject to exert forces to be measured in any direction, and at any location within the reach of the subject.

Data acquisition may be effected in any convenient manner under the control of the system control and data acquisition apparatus 16. Appropriate cables (not shown) connect the cameras, lamps and ergometer with the system control and data acquisition apparatus 16 so that appropriate control signals may be transmitted to the cameras, lamps and dynamometer to effect automatic control of these elements, and data signals may be fed back to the control and data acquisition apparatus for automatic acquisition and processing.

Thus, the data acquired by the position detector 10 may be combined with the data from the force measurement system 14, with the force data correlated to elapsed time and position of the subject effecting the force, with all such data appropriately intermeshed in a series of data frames for further processing by the data processing system 20.

In addition to the previously noted functions, the control and data acquisition system 16 may be utilized to digitize the video position data from the three video cameras as well as the force data from the ergometer. The control system 16 may then serialize the digitized video data, and sequence the video data with the force data for recording and storage 18 for later use, or for direct transmission to the data processing system 20.

Each of the three cameras acquires a complete video frame every 1/60th of a second. The video image is broken into 256 by 256 pixel elements. If, during a particular raster scan, a video camera detects an incandescent lamp in its field of view, the lamp position will be noted within the 256 by 256 element array. Such an identification of the location of the lamp 50, for example, by identification of the horizontal and vertical placement of the lamp image effectively locates the lamp with respect to the camera 34 by means of the projection of a vector 96 on the camera. Similarly, the position of the lamp 50 is identified by proper addressing within the 256 by 256 elements of a raster sweep of the camera 36, for example, effectively locating the lamp by means of the projection of a vector 98 on the camera. Both cameras 34 and 37 are at known locations and orientations relative to the reference lamp 38 and, therefore, the original XYZ coordinate system.

The view from each of the three cameras 32–36 is digitized in this manner. Data may be sampled from each camera in sequence, with each of the cameras obtaining a complete video frame every 1/60th of a second. For minimum delay in data acquisition, all three cameras should be synchronized to the same video horizontal line and frame frequency, with the cameras modified if necessary.

The data stream output by the control and data acquisition system 16 may, for example, consist of a sequence of data frames with each data frame including information acquired during one raster sweep of the three video cameras and information obtained from the ergometer during the three raster sweeps of the cameras. Typically, a data frame may begin with appropriate identifying information followed by the force information. Thereafter, the horizontal location information from each of the three cameras in turn may be provided, and the vertical location information from each of the three cameras follows.

The data processing system 20 utilizes the two-dimensional information from each of the three cameras to form a three-dimensional representation of position and motion. Consequently, as noted hereinbefore, the subject lamp or lamps in use must be viewed by at least two cameras at any time. The front camera 34 will always have the subject lamp in view and, therefore, data from that camera will always be utilized. Whichever of the side cameras 32 and 36 has the subject lamp in view at any moment of data acquisition will supply the second-camera data to be utilized by the data processing system 20. When both side cameras 32 and 36 have the subject lamp in view at the same time, the data processing system 20 will select data for use in calculations and presentations from that side camera to which the subject lamp is closer, for example.

The data processing system 20 may effectively locate a point in space by means of vectors such as 96 and 98 from two of the three cameras. The digitized output from each camera is a pair of values presenting a row number, or scan number, of the video raster scan, and a time value corresponding to the relative position along an individual scan. The combination of row and time values defines a unique ray between the lamp detected and the approximate center of the video camera lens. The row number is proportional to the slope of the ray projection onto a vertical plane aligned with the video camera axis, or field of view center line. The time value is proportional to the slope of the ray projection onto a horizontal plane aligned with the camera axis. For the front camera 34 in FIG. 3 for example, the vertical plane in question could be the plane containing the Y and Z axes, and the horizontal plane in question could be XY plane. The row and time reference values for each camera are the corresponding digitized values of row and time associated with the calibration lamp system origin lamp 54.

When two cameras have been selected for providing data as to the location of a particular lamp, the data processing system 20 may use the digitized data from the two cameras to determine the (X,Y) coordinate values of the lamp in question relative to the XYZ frame of reference. While any type of coordinate system may be utilized, with the cameras oriented in an orthogonal system as illustrated in FIG. 5, for example, the (X,Y) coordinate values for the subject lamp 50 in FIG. 5 may be determined from a simultaneous solution of the equations describing the two observed rays projected onto the XY plane. As noted, the rays in question effectively correspond to the vectors 96 and 98. The equations of the two ray projections are:

$$(X-Y1)/(X-X1)=M1 \qquad (1)$$

and $$(Y-Y2)/(X-X2)=M2 \qquad (2)$$

where:

(X,Y) gives the rectangular coordinates of the subject lamp 50;

(X1,Y1) gives the rectangular coordinates of the front camera 34;

(Yx,Y2) gives the rectangular coordinates of the side camera 36;

M1 is the slope of the ray (vector 96) as determined by the raw digitized data from the front camera 34; and M2 is the slope of the ray (vector 98) as determined by the raw digitized data from the side camera 36.

The position of the subject lamp 50 above or below the XY plane, that is, the Z coordinate of the lamp, may be determined by means of data obtained from either of the cameras used. For example, Z may be determined from the following relationship:

$$(Z-Z1)/D1=S1 \qquad (3)$$

where:

Z is the vertical position of the subject lamp 50;

Z1 is the vertical position of the front camera 34;

D1 is the distance from the lamp to the chosen camera as projected onto the camera axis; and S1 is the slope in the vertical plane between the center line of the field of view of the front camera 34 and the ray from the lamp.

Compilation of (X,Y,Z) coordinate values for a moving subject lamp provides a plot of a body portion trajectory, which may be displayed in tabular form, or by projection on a plotter, or by any suitable means.

Velocity and acceleration of a subject lamp reflecting bodily motion may be calculated using coordinates of successive points in space occupied by the lamp. In FIG. 4 four points are identified by their coordinate values relative to the XYZ coordinate system. The velocity of the subject lamp at each point may be calculated by an appropriate and conventional means. Similarly, the acceleration of the subject lamp may be determined by known methods. If the time interval between determinations of successive position points is short such that $(XYZ)=(X_2-X_1, Y_2-Y_1, Z_2-Z_1)$ is small, for example, then components of the velocity vector $V_1$ may be closely approximated by $\Delta(X,Y,Z)/\Delta T$. Acceleration $d^2(X,Y,Z)/dt^2=dv/dt$ may be derived from changes in velocity vector components $(\Delta V_1 - \Delta V_2)$, etc., between the points $(X,Y,Z)_{1,2}$ by division by corresponding time increments, giving essentially continuous position, velocity and acceleration values for the point or points under study.

In cases wherein two or more subject lamps are utilized to track and record the position and motion of several points of a subject body, the foregoing data processing to obtain position, velocity and acceleration of the subject lamps may be effected for all such lamps. Then, the data processing system 20 provides information descriptive of, for example, the orientation of a human forearm as the hand is moved along a path.

The addition of the values of force generated by a body at the various points at which position data is acquired completes the characterization of the bodily motion.

For a given subject body, essentially an infinite variety of studies can be made of bodily motion and function capability using the ergometer-equipped kinesimeter of the present invention. Several studies are, in general, particularly meaningful and advantageous. For example, to evaluate hand and arm motion and function capabilities, a single subject lamp may be fastened to the hand of a subject, as indicated in FIG. 5 for example. The subject then makes repeated sweeps of the arm and hand, moving the hand over the areas of maximum reach in all quadrants. FIG. 11 shows two views of a space-suited subject 100 effecting such maximum reach sweeps in an orderly fashion with the left arm and hand. The lines 102 are representative of the vertical arm sweeps or point trajectories. The sweep lines also trace out the reach of the arm along the suit and helmet. Thus, a complete, closed envelope is determined by the large number of points in space successively occupied by the subject lamp. The reach envelope is determined by the positions of the subject lamp at extreme reach. A continuous sheet would result from enclosing the maximum reach by an infinite number of hand sweeps, or trajectories. Several techniques may be employed for approximating the reach envelope, utilizing a sufficient number of position points.

One technique for approximating a reach envelope is illustrated in FIG. 8. A right arm reach strophosphere shown generally at 106 is generated by connecting maximum reach position points 108 with straight lines 110. Such a construction may be effected, for example, by use of appropriate computer software.

Reach envelopes may also be constructed by fitting curves to the points obtained by extending the body portion under investigation. A variety of curve fitting techniques are available, and generally may be effected either manually or by use of computers.

By way of example rather than limitation, reach envelopes may be evaluated by considering the intersections of such envelopes with planes or other surfaces. In FIG. 12 the space-suited subject 100 is shown with a right arm and hand reach envelope 112 indicated. In one view of FIG. 12 a plurality of horizontal planes 114 is illustrated, with solid curves of intersection with the envelope 112 shown. In the other view of FIG. 12 vertical planes 116 are illustrated intersecting the envelope 112.

The relationship between reach envelopes and intersecting planes may be further appreciated by reference to FIGS. 6 and 7. A right arm and hand reach envelope for a subject 118, with reference point 120, is indicated by sweep lines 122. A horizontal plane 124 is considered at a level just below the shoulders of the subject 118. Points of intersection 126 of sweep lines 122 with the surface 124 are illustrated in FIG. 6. During an actual subject study it is possible that not all motions of the body portion under investigation will be effected at the intended extreme extension. Consequently, the points of intersection 126 include a scattering of points not representative of the intended extreme reach, as well as a large number of points truly reflecting the extended reach. The points lying along the periphery of the collection of points in the plane 124 may be connected by a smooth curve by any conventional technique, including manual techniques for example. The resulting smooth curve 128 is the line of intersection of the envelope of maximum right arm and hand reach of the subject 118 in the horizontal plane 124. The area 130, shown shaded in FIG. 7, is the area in the plane 124 all of whose points may be reached by the subject body portion under investigation.

Points of intersection of sweep lines with a selected plane may be identified by means of the data processing system 20. For example, the selected plane may be identified mathematically in relation to the XYZ coordinate system. As the data processing system 20 receives the position data in the data stream and determines the location of the various points of the subject lamp or lamps, the data may be continually examined to identify points which lie on the selected plane. Where adjacent position points in the data stream are determined mathematically to lie on opposite sides of the selected surface, the data processing system 20 may perform an interpolation to determine the cartesian coordinates of the intersection between the path of the moving subject light and the specified surface.

Figure 13:
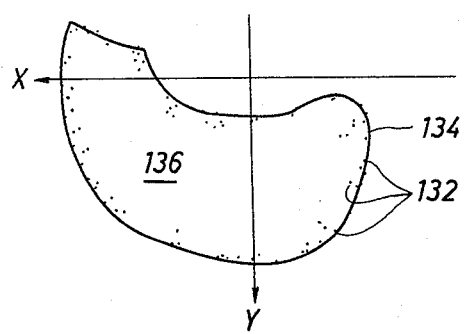
FIG. 13 is a plan view of the intersection of a horizontal plane with a reach envelope as may be constructed from intersection points.

In FIG. 13 position points 132 are located in the XY plane, for example, indicating the points of intersection of the plane with subject lamp trajectories. A continuous smooth curve 134 connecting the generally peripheral points identifies the intersection of the corresponding reach envelope and the XY plane. The area 136 within the closed curve 134 then indicates the area in the XY plane which can be attained by the subject body portion under investigation.

The present invention thus provides for the establishment of reach envelopes, that is, identification of regions of extreme motion which may be measured and approximated by either an array of points, or interpolations made between points. Further, the envelope data may be stored by conventional means, and serve as a practical description of a subject body's performance potential that is characteristic of the body. Furthermore, envelopes and iso-contours for velocity and acceleration along selected directions may be generated and/or stored in the same manner as reach envelopes. Such velocity and acceleration presentations further define the functional capability of a subject body by indicating the ability of the body portion under investigation to obtain identifiable velocities and accelerations at certain locations, and in specified configurations.

Figure 15:
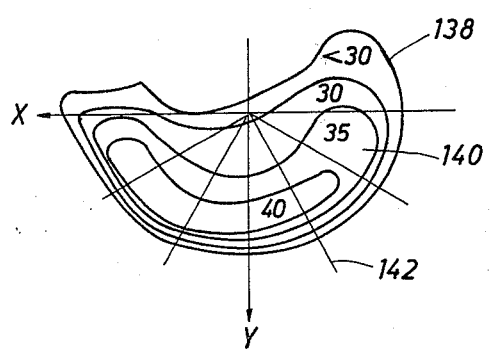
FIG. 15 is a force plot constructed from a horizontal plane intersecting iso-force envelopes.

Force and torque vectors may also be obtained by use of the ergometer, reflecting the values of such quantities which can be generated within a specified reach envelope. Appropriate displays may be made for such force and torque values. For example, a subject body may generate either push or pull forces along a series of radials projecting through a reach envelope. By extrapolation a series of iso-force envelopes may be developed, as indicated in FIG. 15. The closed curves 138 are lines of intersection of the XY plane with several iso-force envelopes. Each of the continuous curves 138 encloses an area 140 within which the subject body may generate a force or torque of value at least as large as the minimum numerical value indicated (in unspecified units). Thus, for example, within the smallest continuous curve 138 the subject body may exert forces along radial lines 142 of quantitative value 40 in selected units. Within the next larger area the maximum force the subject body may generate along the radial lines 142 is 35 of the same units. Within the largest closed curve 138 the subject body may not exert a force as large as 30 equivalent units.

In addition to maximum reach envelopes, ranges and trajectories, and other functional envelopes, contours and range presentation, including velocity, acceleration and force presentations, various other selected envelopes, ranges and iso-contours reflecting specified characteristics may be generated. For example, while a subject body may extend its reach over a large region, there may be portions of that region which the subject body can attain only with considerable difficulty. Other regions within the maximum reach envelope may be attained by the body conveniently and, in the case of a living subject, with no undue fatigue. The present invention may be utilized to identify and distinguish the various reach regions.

Figure 14:
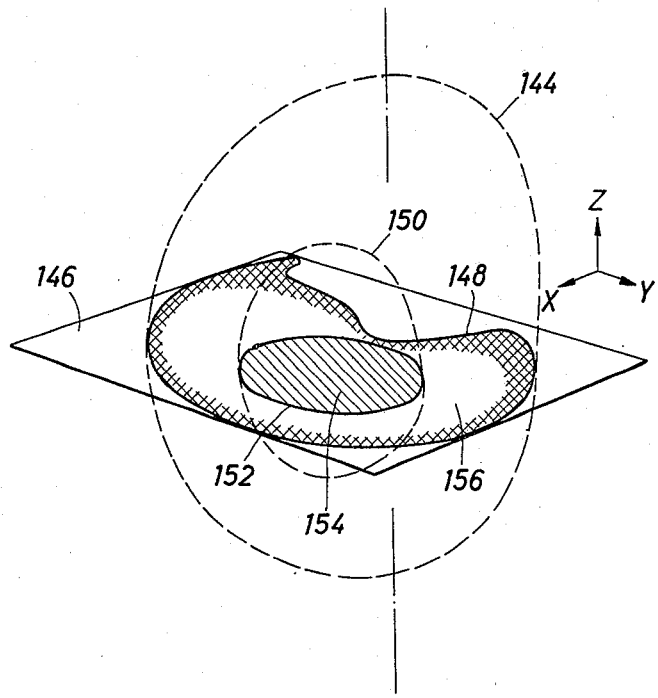
FIG. 14 is a perspective view of a maximum reach envelope and a functional reach envelope, intersected by a plane.

In FIG. 14 a maximum reach envelope 144 is intersected by a horizontal plane 146 along a closed curve 148. The plane 146 further intersects a functional reach envelope 150, contained within the maximum reach envelope 144 and characterized by the ability of the subject body to perform effectively within selected parameters within the region of the functional reach envelope. For example, the functional reach envelope 150 may contain the region within which the subject body may generate forces of at least a selected minimum value, and/or within which the subject body portion may move at specified velocity values. In terms of the subject body performance, the functional reach envelope 150 may define the region in which the subject body portion may move comfortably without undue fatigue. All regions within the maximum reach envelope 144 but exclusive of the functional reach envelope 150 may be attained by the subject body portion, but not within the specified parameters.

The horizontal plane 146 intersects the functional reach envelope 150 as indicated by the continuous curve 152 enclosing the area 154. The area within the continuous curve 148 defining the intersection of the maximum reach envelope 144 and the plane 146, but exclusive of the area 154 within the continuous curve 152, may be identified as the restricted reach area 156. This is an area in the XY plane which the subject body may attain but without coming within the specified function parameters which are used to define the functional reach envelope 150. Area 154 in the XY plane within the functional reach envelope 150 defines the functional reach range in that plane.

Additional studies may be conducted. For example, reach envelopes for left and right arms on a subject body may be generated, and the overlap region between the envelopes noted. The overlap region of the two envelopes establishes an envelope reflective of the reach of both hands, for example, and within which bimanual activity is available. Generally, functional bimanual reach envelopes of any desired parameters may be established.

The performance data processed by the data processing system 20 and reflective of the functional capability of a given subject body may be automatically or manually interfaced with specific areas of applications. Such interfacing may be done graphically or analytically, for example. Additionally, the data gathering and processing means of the present invention may be utilized to obtain and analyze reach and function measurements for a given population in a specified configuration, for example. Output plots reflecting the data gathered from the selected population may then be overlayed on either existing or planned layouts of an environment, such as a work area or machine configuration. Such interfacing of anthropomorphic and environmental data may then be examined to ensure that the selected environment can accommodate the performance capabilities of the selected population, for example. Alternatively, for example, such interfacing may be utilized to identify those portions of the population which are capable of functioning as desired in the selected environment. Several existing computer programs are available which intersect derived models of humans with machine environments.

The present invention may be effected in a variety of configurations. The construction and functioning of the invention may be subdivided with consequent reduction in machine complexity. For example, the data processing system 20 may be provided by several integral computer elements designed for specific tasks rather than by a general purpose computer. The selection of data processing, analysis and output facilities may be determined based on the needs of particular applications. Considerable simplifications would result, for example, if only trajectory tracking were utilized without carrying out the generation of envelopes and other data formats. Such simplification of the data processing and handling functions generally allows for greater on-line capability of the system. The data collection elements of the invention, including the position detector 10, clock 12, force measurement system 14 and system control and data acquisition means 16 may be located remotely from the remainder of the apparatus, with communication between the separated elements effected by any appropriate means.

The data input facilities of the present invention may be varied as circumstances permit and/or dictate. Any variety or arrangement of detector instrumentation which provides the information of interest, directly or indirectly, could be used to provide the position detector 10 and/or the force measurement apparatus 14, for example. A considerable variety of position detectors are known. Further, accelerometers could be used to derive velocity and acceleration values directly, and to derive forces indirectly utilizing known inertial and other properties opposing movement of the subject body.

The present invention may be utilized to study any type of body motion, including complex machine motion and especially motion in robotics. Further, the number of points on a subject body which may be tracked and studied according to the present invention are effectively limitless, being determined, for example, by practical considerations and the nature of a particular study desired.

The present invention provides a practical system for automatically gathering complete, three-dimensional, kinesimetric data on human and machine subjects, for example. The nature and format of the data acquired are such that the data may be utilized automatically and directly to study performance and environment design. The present invention may be utilized to determine complete motion parameters of subject bodies and body portions in terms of position, velocity, acceleration and/or force, or any combination thereof. Individual and characteristic data sets may be derived describing bodily motions, and presented in the form of envelopes of reach, functional reach, velocity, acceleration, and force, for example. Particular motions can also be tracked or recorded in terms of any or all of the aforementioned parameters. Displays, diagrams or other data may be generated of any selected region or aspect of the aforementioned data sets, including a planes, volumes, regions or trajectories, and which may be either manually derived or done so by automatic means. The data may be manually or automatically interfaced with external physical environmental information, and graphic displays or other aspects of the interaction automatically or manually generated. Particular aspects of motion, such as trajectories of one or more body segments, may be studied either alone or interacting with a physical environment.

The present invention for the first time provides a practical means for gathering and storing large amounts of exact, individual anthropometric data which can be used from the beginning of a design process in contrast to previous methods, such as making mock-ups and using individuals to function and fit test the mock-ups, or first building an environment and then testing it with real subjects. Further, the present invention provides a practical means for collecting and storing data reflecting the motions of a body, compared to the previously available static measurements utilized in anthropometry.

The foregoing disclosure and description of the invention is illustrative and explanatory thereof, and various changes in the method steps as well as in the details of the illustrated apparatus may be made within the scope of the appended claims without departing from the spirit of the invention.

I claim:

1. Apparatus for determining functional capability of bodies comprising:
   a. position detector means for sensing the location of such a body in three dimensions;
   b. force detector means for sensing force exerted by said body;
   c. data acquisition means for acquiring information of positions of said body in three dimensions as a function of time from said position detector means and force exertion information from said force detector means; and
   d. means for presenting information acquired by said data acquisition means descriptive of the limits of a selected envelope.

2. Apparatus as defined in claim 1 further comprising data processing means for operating on information acquired by said data acquisition means.

3. Apparatus as defined in claim 1 further comprising means for storing information so acquired by said data acquisition means.

4. Apparatus as defined in claim 1 wherein said position detector means and said force detector means may be operated simultaneously to sense location of, and force exerted by, said body, respectively.

5. Apparatus as defined in claim 1 wherein said force detector means comprises ergometer means.

6. Apparatus as defined in claim 1 further comprising means for comparing said position information and force exertion information with information characteristic of a selected environment.

7. Apparatus as defined in claim 1 wherein said position detector means comprises optical sensor means.

8. Apparatus as defined in claim 7 wherein said optical sensor means comprises at least two video cameras arrayed generally in a plane.

9. Apparatus as defined in claim 1 wherein said data acquisition means further comprises means for digitizing detection signals from said position detector means and from said force detector means.

10. Kinesimetric apparatus comprising:
    a. a plurality of video cameras arranged in a plane and oriented to sense the position and movement of a subject body so that at least two of said video cameras may so sense said body at any time;
    b. means for acquiring output signal from said video cameras carrying information of the position and motion of said subject body; and
    c. means for reducing said output information into position trajectory and reach envelope information.

11. Apparatus as defined in claim 10 further comprising ergometer means for acquiring information of force exerted by said subject body.

12. Apparatus as defined in claim 11 wherein said ergometer means comprises dynamometer means.

13. Apparatus as defined in claim 11 wherein said data processing means further comprises means for combining said force information and said position information.

14. Apparatus as defined in claim 10 further comprising means for interfacing said output information with information characteristic of a selected environment.

15. A method of determining functional capability of bodies comprising the following steps:
    a. providing a detector for sensing the location of such a body in three dimensions as a function of time;
    b. providing data acquisition means for acquiring data from said detector including information of the position of said body as a function of time;
    c. sensing the location of said body as a function of time by said detector;
    d. so acquiring said information from said detector by said data acquisition means;
    e. reducing said information so acquired; and
    f. so processing information from said detector sensing positions assumed by said body at the limits of a selected reach envelope.

16. A method as defined in claim 15, further comprising the additional steps of so processing said reach envelope information to generate corresponding reach envelope data.

17. A method as defined in claim 16 further comprising the additional steps of processing said position information to generate data defining a plane intersecting said reach envelope.

18. A method as defined in claim 15 further comprising the additional steps of so processing information from said detector sensing positions assumed by said body at the limits of a maximum reach envelope, a functional reach envelope and a restricted reach envelope.

19. A method as defined in claim 15 further comprising the additional steps of processing said position information to determine information describing the velocity of said body motion as a function of time.

20. A method as defined in claim 15 further comprising the additional steps of processing said position information to determine acceleration information of said body motion as a function of time.

21. A method as defined in claim 15 further comprising the additional steps of interfacing said information concerning positions of said body with information characteristic of a preselected environment.

22. A method as defined in claim 15 further comprising the additional steps of providing an ergometer and sensing the position and motion of said body as said body effects force on said ergometer.

23. A method as defined in claim 22 further comprising the additional steps of acquiring information from said ergometer concerning said force exerted on said ergometer by said body.

24. A method as defined in claim 23 further comprising the additional steps of processing said force information and said position information and generating data reflecting the generation of force by said body as a function of position.

25. A method as defined in claim 24 further comprising the additional steps of interfacing said information concerning force generated by said body and position of said body with information characteristic of a selected environment.

26. A method as defined in claim 23 further comprising the additional steps of processing information from said detector and from said ergometer descriptive of the limits of a selected envelope.

27. A method as defined in claim 15 further comprising the additional steps of reducing said position information to obtain information of the velocity and acceleration of said body, and interfacing said position, velocity and acceleration information with information characteristic of a selected environment.

* * * * *